United States Patent
Polkus et al.

(10) Patent No.: US 6,439,769 B1
(45) Date of Patent: Aug. 27, 2002

(54) AUTOMATED RECEPTOR TRACKING TO DIAGNOSTIC SOURCE ASSEMBLY

(75) Inventors: Vincent Stanley Polkus, Delafield; Manfred David Boehm, Waukesha; Xianfeng Ni, Milwaukee, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/681,315

(22) Filed: Mar. 16, 2001

(51) Int. Cl.$^7$ ................................................. H05G 1/02
(52) U.S. Cl. ....................... 378/205; 378/167; 378/197
(58) Field of Search ................................. 378/167, 177, 378/187, 189, 193, 195, 196, 197, 198, 205

(56) References Cited

U.S. PATENT DOCUMENTS

| | | | | |
|---|---|---|---|---|
| 3,492,482 A | * | 1/1970 | Forsyth ....................... | 250/424 |
| 5,572,567 A | | 11/1996 | Khutoryansky et al. .... | 378/197 |
| 5,734,694 A | | 3/1998 | Khutoryansky et al. .... | 378/197 |
| 5,940,470 A | * | 8/1999 | Palm-Plessmann et al. . | 378/193 |
| 6,302,580 B1 | * | 10/2001 | Dwyer et al. ............... | 378/196 |

* cited by examiner

Primary Examiner—David P. Porta
(74) Attorney, Agent, or Firm—McAndrews, Held & Malloy, Ltd.; Peter J. Vogel; Michael A. Dellapenna

(57) ABSTRACT

A system and method for automatically positioning an image receptor based on the position of a manually positioned diagnostic source assembly in an X-ray imaging device is provided. In a preferred embodiment of the automated tracking system, an operator manually positions a diagnostic source assembly (DSA) over the area of a patient to be imaged. Sensors in the diagnostic source assembly transmit the position of the DSA to a system controller. The system controller then calculates an optimal position of an image receptor based on the position of the DSA. Once the optimal position is calculated, the system controller sends the optimal position to a motor drive, which positions the image receptor in the calculated optimal position. Position sensors in the image receptor then send positional data of the image receptor to the system controller, which verifies that the image receptor is in the calculated optimal position. If the operator wishes to manually adjust the image receptor, they may override the motor drive and do so. The automated tracking system provides for reduced total imaging time and increased cost effectiveness over prior X-ray imaging systems by reducing the number of retakes required to obtain a satisfactory X-ray image. Reducing retakes also results in decreased exposure to radiation by the patient being imaged which is healthier to the patient.

22 Claims, 3 Drawing Sheets

AUTOMATED RECEPTOR TRACKING TO DIAGNOSTIC SOURCE ASSEMBLY

BACKGROUND OF INVENTION

The present invention generally relates to a system and method for controlling the position of a radiographic device. More particularly, the present invention relates to a system and method for automatically positioning an image receptor based on the position of a manually positioned diagnostic source assembly in an X-ray imaging device.

Radiographic imaging systems are used for a wide variety of applications in the medical field. One example of a radiographic imaging system used in medicine is an X-ray imaging system. X-ray imaging systems are typically used for diagnostic purposes in the medical field. Typical X-ray imaging systems operate by transmitting X-radiation or X-rays through a patient's body using a diagnostic source assembly ("DSA"). The DSA is typically a device that is capable of transmitting X-rays through the body of a patient. The position of the DSA is typically adjustable and the DSA is generally placed over the area of a patient's body that is being imaged. Once properly positioned, the X-rays transmitted through the patient's body by the DSA are more absorbed by dense structures in the body such as bones, and less absorbed by less dense structures such as tissue and organs. The X-rays passed through the patient's body are then typically received by an image receptor located beneath the patient. Typically, the image receptor is comprised of either an X-ray film or a digital solid state detector.

In order to achieve an X-ray image with sufficient information and contrast to provide a doctor with the diagnostic information needed, precise alignment of the DSA and the receptor often needs to be achieved. Typically, the DSA projects a beam of X-rays toward the image receptor surface and through body structure of the patient being imaged. The area of projected X-rays that is incident on the image receptor defines the active imaging area (AIA). Generally, the X-ray beam field or field of view (FOV), which is the intersection of the projected beam and the image receptor plane, must be coincident with, or lie within, the boundaries of the image receptor surface in order to avoid loss of image data. The FOV may be adjusted by rotating or tilting the DSA to vary the direction of the projected X-ray beam, and also by operating a collimator to vary the width and length dimensions of the X-ray beam. Further adjustments may also be made by linear translation of the DSA or the image receptor.

When the DSA is oriented so that the X-ray beam is directed in perpendicular or orthogonal relationship to the image receptor plane, the image receptor may be located directly below the DSA. However, X-ray technicians or operators may need to angulate the DSA with respect to the image receptor, that is, rotate or pivot the DSA so that the beam is not projected perpendicular to the image receptor. Angulation of the DSA may be desirable, for example, to ensure that the beam passes through a specific body structure of the patient, or to avoid imaging specific structures. As the DSA becomes increasingly angulated, the image receptor typically needs to be positioned at a location offset from the position of the DSA in order to receive the X-rays. Typically, the greater the degree of angulation the DSA is from perpendicular to the image receptor, the greater the offset between the image receptor and the DSA need to be. Therefore, in order to ensure the image receptor receives the X-rays from the DSA, the operator typically needs to precisely position the image receptor so that it is in the X-ray beam's FOV.

In the absence of optimal or appropriate alignment of the DSA and the image receptor, anatomical cutoff may occur during the imaging process. That is, the bodily structures intended to be imaged may not be completely imaged due to the incorrect offset between the DSA and the image receptor. Anatomical cutoff may necessitate that the imaging be repeated, which may increase procedure cycle time, raise examination costs, and expose the patient to higher levels of net radiation.

In typical prior art systems, efforts to attain the precise alignment of the DSA with the image receptor desired for successful imaging has been attempted by one of two methods. The first method typically used to align the DSA and image receptor is through direct alignment. That is, physically attaching the DSA to the image receptor in the desired alignment. The second method typically used to align the DSA and image receptor is through indirect alignment methods. That is, positioning the DSA and the image receptor individually when they are not attached together. Both methods are further described below.

In typical X-ray imaging systems that utilize direct alignment of the DSA and the image receptor, the DSA and the image receptor are physically attached to each other by a rigid structure. The DSA is typically attached in a perpendicular alignment to the image receptor so that the X-ray beam transmitted by the DSA will be transmitted directly into the flat plane of the receptor. In direct alignment systems, the DSA and the image receptor are typically not moveable or able to be repositioned by an operator or X-ray technician. Because of the rigidly fixed positioning of the DSA and the image receptor, X-ray imaging systems that utilize direct alignment may suffer from a number of drawbacks.

One drawback that may occur in direct aligned X-ray imaging systems is lack of flexibility in positioning of the system by the operator. That is, when the position of the system is fixed, the operator may have to adjust the patient's position in order to get an image. During imaging procedures it may be more difficult to adjust the patient to the X-ray system than it is to adjust the X-ray system to the patient. However, in a direct aligned system only limited adjustment of the system is possible. Therefore, if patients are required to hold difficult or uncomfortable positions in order to fit into the X-ray imaging system, bad images may be generated and frequent retakes may be required. Requiring frequent retakes may often be time consuming and may expose the patient to excess radiation. Additionally, with direct aligned X-ray imaging systems, retakes may be further complicated by patient access. That is, once a determination has been reached to retake an image, the patient may have exited the system or may have to be re-scheduled. Also, direct aligned X-ray imaging systems are less desirable because the systems are typically quite complex and costly.

In order to overcome some of the drawbacks related to the rigid inflexibility of direct aligned systems, some prior art X-ray systems have utilized indirect alignment methods. That is, the DSA and the image receptor are not physically attached to each other and may be individually positioned by an operator. Individually positioning the DSA and the image receptor may help give the operator more flexibility and may allow for better patient comfort than direct aligned systems. Typically positioning of the DSA and receptor in indirect aligned systems has been achieved by one of two methods. The first method typically used in indirect alignment systems involves manual positioning of both the DSA and the image receptor by an operator. The second method typically used in indirect alignment systems is motorized positioning of both the DSA and the image receptor.

In typical indirect alignment systems manually positioned, an operator physically positions the DSA and the image receptor by hand. Generally, at first, the DSA may be manually positioned by the operator in a position appropriate for the area of the patient's body being imaged. Next, the patient is typically positioned so that the area of the patient's body to be imaged is comfortably positioned with respect to the DSA. Finally, the image receptor may be manually positioned by the operator in the proper alignment with the DSA. The operator may use a visual light field projected by the DSA on to the patient or receptor to judge where the DSA should be positioned with respect to the patient and the image receptor. Once the operator concludes that the DSA and the image receptor have been optimally aligned, the image may be taken. While the manual positioning of the DSA and the imaging receptor by the operator may allow much greater flexibility to the operator than in direct alignment systems, a number of drawbacks with manual positioning may result.

One drawback that may occur in manually positioned indirect alignment systems is inconsistent alignment. Because the DSA and the image receptor are both manually positioned by the operator, the operator must judge when the DSA and image receptor are in optimal alignment. While the visual light field discussed above may help aid the operator in their judgment, it still may be difficult for the operator to precisely determine when the DSA and image receptor is in optimal alignment. Inconsistent alignment of the DSA and the receptor by the operator may result in poor quality images, anatomical cutoff, or may require frequent retakes. As mentioned above, frequent retakes may increase imaging time and expose the patient to excess radiation.

An additional drawback which may occur in manually positioned indirect alignment systems is the increased time required to position the DSA and the image receptor. Because the operator must judge and manually position both the DSA and the image receptor, proper alignment may require some time. The operator may have to position and then reposition the DSA, the image receptor, or both numerous times before an optimal alignment may be achieved. Therefore, the "trial and error" nature of manually positioning both the DSA and the image receptor may increase the time required to take good images. Increased time may result in reduced throughput of the imaging department of the medical facility, which may be busy during a typical day.

The second method typically used in indirect alignment systems is motorized positioning of both the DSA and the image receptor. That is, the operator uses controls to position a motorized DSA and a motorized image receptor into proper alignment with each other. In typical motorized positioning systems, the operator may use the controls to position the motorized image receptor into a position appropriate for the area of the patient's body being imaged. Next, the patient is typically positioned so that the area of the patient's body to be imaged is comfortably positioned over the image receptor. Finally, the motorized DSA may be positioned by the operator using the controls in the proper alignment with the image receptor over the area of the patient's body to be imaged. Once the operator concludes that the DSA and the receptor have been optimally positioned, the image may be taken. While the motorized positioning of the DSA and the image receptor by the operator may allow greater precision to the operator than in manually positioned indirect alignment systems, a number of drawbacks with motorized positioning may result.

One drawback that may be present in motorized positioning systems is loss of freedom of motion of the DSA and the image receptor. That is, the range of motions available to the motorized DSA and the motorized image receptor may be less than the range of motion available to the manually positioned system. Having reduced range of motion may limit the ability of the operator to quickly and efficiently align the DSA and the image receptor. The operator may have to adjust the patient to compensate for the reduced range of motion that may be available to the motorized positioning system. Having to adjust the patient and not being able to position the DSA and the receptor in exactly the desired position may result in poor images and the need for retakes. As described above, poor imaging and retakes may have adverse effects on the patient and hospital throughput.

Another disadvantage that may be present in motorized positioning systems is the amount of time required to position the system. Typically, positioning the DSA and the image receptor by motorized control is slower than manually positioning the DSA and the receptor, particularly when the displacements are large. Thus, if multiple images from different angles or retakes are required, the increase in imaging time due to the motorized positioning of the DSA and the image receptor may be significant. As mentioned above, increasing the imaging time may lead to reduced throughput and back-ups in the imaging department of busy hospitals. Additionally, motorized positioning systems fail to address the various preferences or needs of an operator to move the positioning system at a slower or faster rate, as desired. That is, motorized positioning systems may not provide continuously variable of proportional speed control as desired by an operator.

Thus, a need exists for a positioning control system for a medical imaging device, such as an X-ray imaging device, that combines the optimal alignment properties of a direct alignment system with the flexibility of an indirect alignment system. A need further exists for a positioning control system that allows for quick and precise alignment of a diagnostic source assembly and an image receptor.

SUMMARY OF INVENTION

The preferred embodiment of the present invention provides a system and method for automatically positioning an image receptor based on the position of a manually positioned diagnostic source assembly (DSA) in an X-ray imaging system. In operation, a patient whom the X-ray imaging will be performed on is placed on the examination table of the imaging system. An X-ray technician or operator then manually positions the DSA over the area of the patient's body to be imaged. Once the DSA is manually positioned in the proper location by the X-ray technician, position sensors in the DSA transmit the lateral, longitudinal, vertical, and angular orientation of the DSA to a system controller. The system controller calculates the optimal position of the image receptor based on the position of the DSA. The system controller then transmits the optimal position to a motor drive that automatically positions the image receptor in the optimal position. Once the image receptor has been positioned in the optimal position by the motor drive, sensors in the image receptor transmit the positional data of the image receptor to the system controller. The system controller then verifies that the image receptor has been positioned in the correct location. If the system controller determines that the image receptor has been properly positioned, the X-ray imaging may then occur. If the system controller determines that the image receptor has not been properly positioned, the X-ray technician may override the motor drive and manually position the image receptor in the desired location.

DETAILED DESCRIPTION

Figure 1:
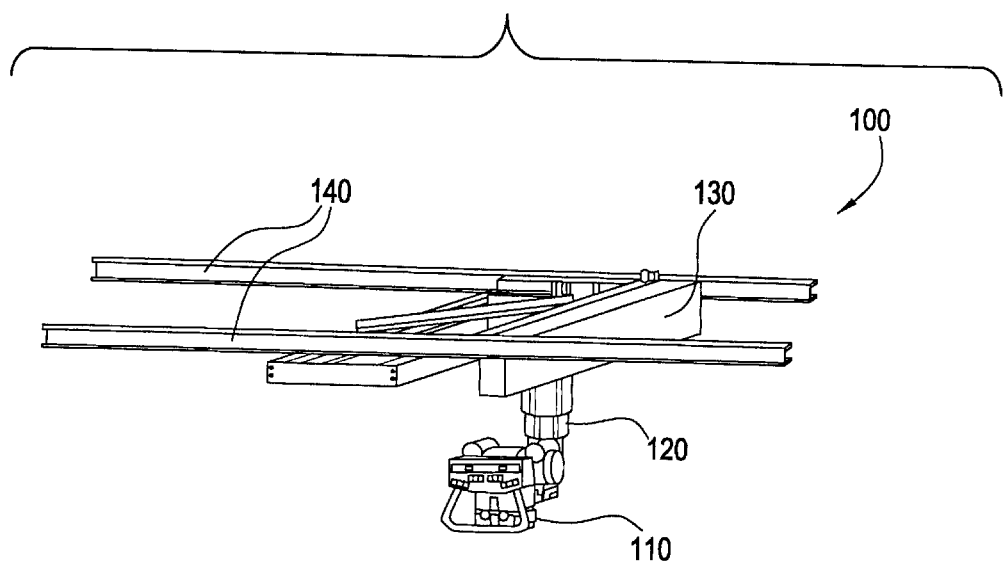
FIG. 1 illustrates an automated receptor tracking system according to a preferred embodiment of the present invention.
Figure 1:
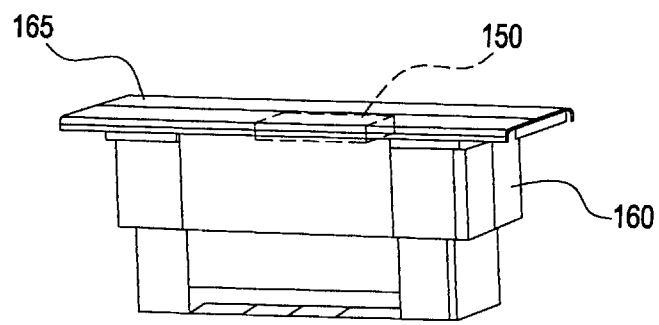

FIG. 1 illustrates an automated receptor tracking system 100 according to a preferred embodiment of the present invention. The tracking system 100 includes a diagnostic source assembly (DSA) 110, a DSA crane 120, a crane mount 130, crane mount guide bars 140, an image receptor 150, an exam table 160, and a table top 165.

The DSA is preferably attached to the lower end of the DSA crane 120 as illustrated in FIG. 1. The upper end of the DSA crane 120 is then preferably attached to the crane mount 130. The crane mount 130 is held in position by the crane mount guide bars 140. The crane mount guide bars 140 are preferably attached to the ceiling or upper wall of a medical imaging room. Located directly beneath the crane mount guide bars 140 on the medical imaging room floor is the exam table 160. Attached to the top of the exam table 160 is the table top 165. Located in the exam table 160 directly beneath the table top 165 is the image receptor 150.

In a preferred embodiment of the tracking system 100, the DSA 110 includes position sensors to preferably detect and transmit the lateral, longitudinal, vertical, and angular orientation of the DSA 110. The image receptor 150 also contains position sensors to detect and transmit the image receptor height and longitudinal position. The position data detected by the sensors in the DSA 110 and the sensors in the image receptor 150 is preferably transmitted to a system controller (not shown). The system controller is used to analyze the sensor data and compute an optimal alignment position of the image receptor 150 relative to the position of the DSA 110 prior to taking an image. In addition to the position sensors, the image receptor 150 also includes a motor drive (not shown) that is used to adjust the longitudinal position of the image receptor 150. The motor drive of the image receptor 150 is preferably controlled by the system controller. After calculating the optimal alignment position of the image receptor 150 relative to the position of the DSA 110, the system controller then transmits the optimal image receptor 150 position to the motor drive.

In operation, a patient is preferably positioned on the table top 165 of the exam table 160. An X-ray technician or operator then manually positions the DSA 110 to a position suitable for imaging the desired area of the patient. The DSA 110 is manually positioned by physically adjusting the DSA 110 to its intended orientation. The DSA 110 is held in its desired position by the DSA crane 120. The DSA crane 120 allows for a full range of motion and angular orientation of the DSA 110. The DSA 110 is preferably manually positioned correctly by using a visual light field projected on the patient by the DSA 110 indicating the area of the patient to be imaged at the current position of the DSA 110. Additional longitudinal positioning may be achieved by sliding the crane mount 130 along the crane mount guide bars 140 as illustrated in FIG. 1.

Once the operator manually positions the DSA 110, the sensors in the DSA 10 transmit the lateral, longitudinal, vertical, and angular orientation of the DSA 110 to the system controller. The system controller then calculates the optimal image receptor 150 alignment and height so that the full desired area of the patient may be imaged without anatomical cutoff. Once the optimal image receptor 150 alignment and height is calculated by the system controller, the system controller transmits the optimal alignment data to the motor drive of the image receptor 150. The motor drive then automatically positions the image receptor 150 in the optimal alignment and height with the DSA 110 as calculated by the system controller. The sensors in the image receptor 150 transmit the position of the image receptor 150 to the system controller so the system controller is able to verify that the image receptor 150 has reached the optimal position. Once the image receptor 150 has been optimally aligned with respect to the position of the DSA 110, the X-ray imaging may be performed. Thus, the tracking system 100 allows the operator to "point and shoot" the X-ray by simply aiming the DSA 110 over the desired imaging area of the patient. The image receptor 150 is automatically tracked to the optimal position by the system controller and motor drive.

If for some reason the operator wants to manually adjust the image receptor 150 as well as the DSA 110, the motor drive of the image receptor 150 may be disengaged. When the motor drive is disengaged, the operator may manually position the image receptor 150 in substantially the same fashion as the manually positioned indirect alignment system described above.

Figure 2:
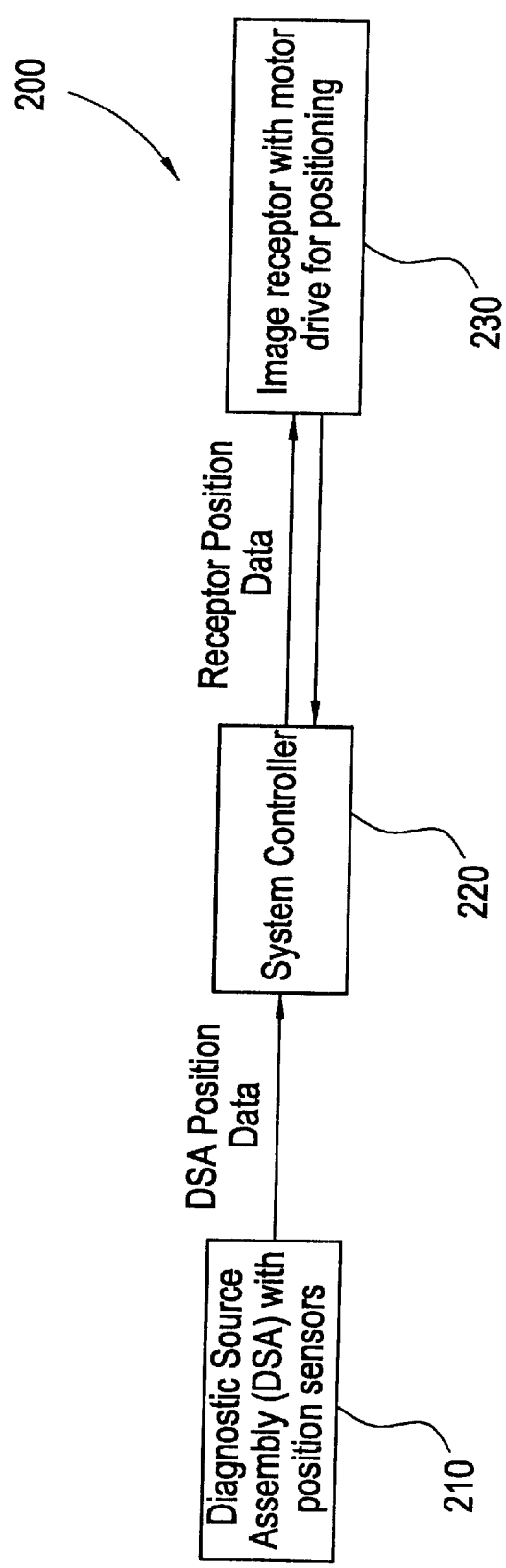
FIG. 2 illustrates a block diagram of an automated receptor tracking system according to a preferred embodiment of the present invention.

FIG. 2 illustrates a block diagram 200 of an automated receptor tracking system according to a preferred embodiment of the present invention. The block diagram 200 includes a diagnostic source assembly (DSA) 210 with position sensors, a system controller 220, and an image receptor 230 with a motor drive.

In operation, the sensors in the DSA 210 preferably transmit the lateral, longitudinal, vertical, and angular orientation of the DSA 110 to the system controller 220. As discussed above with reference to FIG. 1, the system controller 220 receives and analyzes the position data from the DSA 210. Based on the position data received from the DSA 210 when the DSA 210 is manually positioned in the desired location, the system controller 220 calculates the optimal position for the image receptor 230. Once the optimal position for the image receptor 230 is calculated with respect to the position of the DSA 210, the system controller 220 sends the optimal position to the motor drive of the image receptor 230. The motor drive of the image receptor 230 then automatically moves the image receptor 230 to the calculated position. The sensors in the image receptor 230 transmit the position of the image receptor 230 to the system controller so the system controller is able to verify that the image receptor 230 has reached the optimal position. Once the image receptor 230 has been optimally aligned with respect to the position of the DSA 210, the X-ray imaging may be performed.

Figure 3:
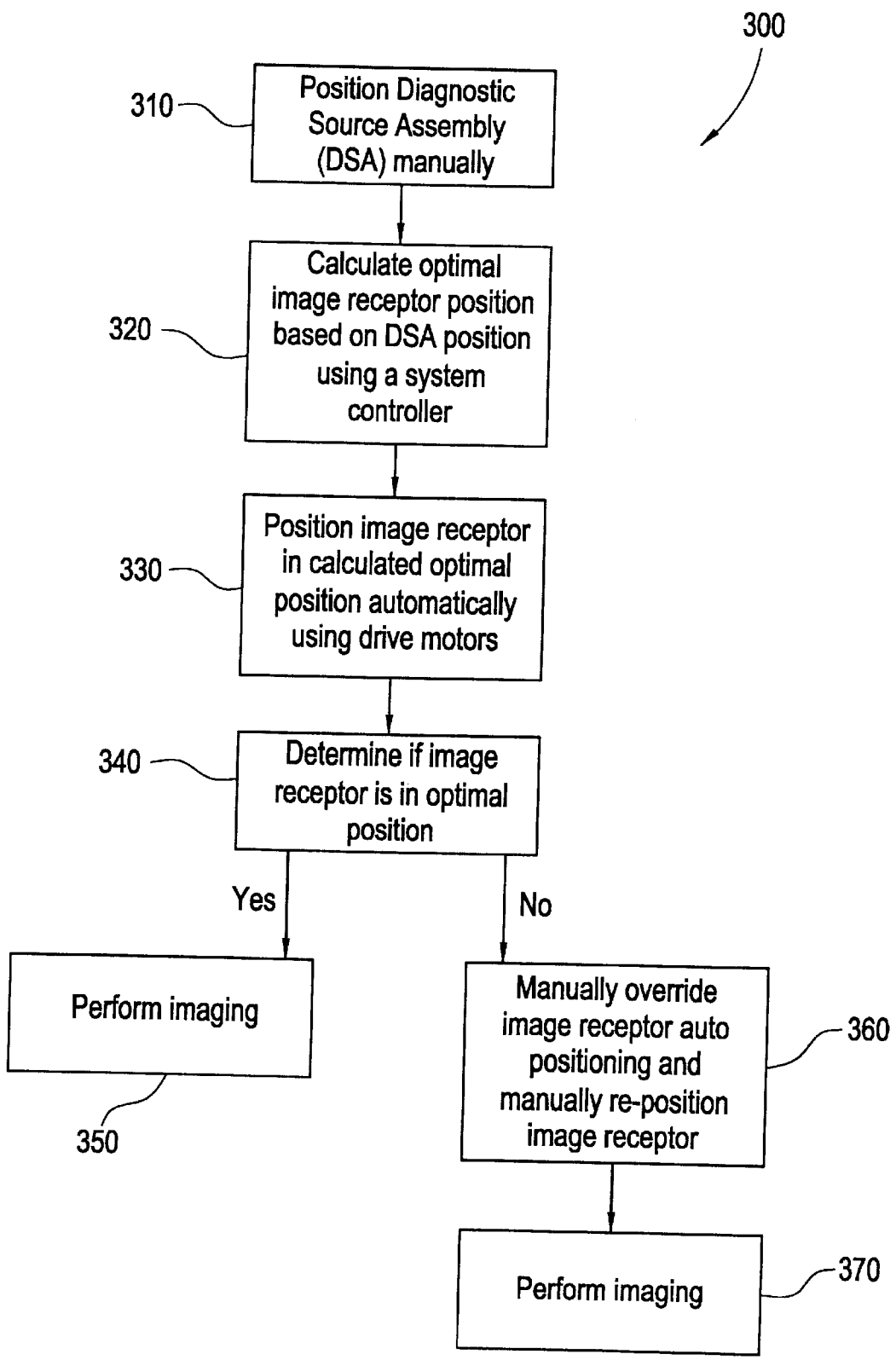
FIG. 3 illustrates a flow chart of an automated receptor tracking system according to a preferred embodiment of the present invention.

FIG. 3 illustrates a flow chart 300 of an automated receptor tracking system according to a preferred embodiment of the present invention. First, at step 310, an operator manually positions the DSA in the desired location. Then, at step 320, the system controller calculates the optimal position for the image receptor based the position data received from the sensors in the DSA. Next, at step 330, the image receptor is automatically positioned in the optimal position calculated by the system controller by the motor drive. At step 340, the system controller verifies that the image receptor has been positioned in the calculated optimal position from the data received from the position sensors in the image receptor. If the position of the image receptor is verified as being optimal, then at step 350, the X-ray imaging is performed. If the position of the image receptor is determined to not be optimal, at step 360, the operator may manually override the image receptor motor drive and manually position the image receptor. If the position of the manually repositioned image receptor is determined to be optimal, finally, at step 370, the X-ray imaging is performed.

In a second embodiment of the present invention, the tracking system 100 may be modified to allow for transverse movement of the image receptor in addition to longitudinal and height movements. In the second embodiment, an additional position sensor is provided in the image receptor to track the transverse position of the image receptor. In operation, the DSA is manually positioned in substantially the same fashion as described above with reference to FIG. 1. However, when the system controller calculates the optimal alignment and height of the image receptor, transverse positioning of the image receptor is also taken into account. Thus, when the system controller sends the optimal calculated position to the motor drive of the image receptor, the motor drive may position the longitudinal position, the transverse position, and the height of the image receptor to the calculated location. Increasing the range of motion of the image receptor to include transverse motion may increase the ability of the tracking system 100 to take complete and accurate images with low attenuation or anatomical cut-off.

In a third embodiment of the present invention, the tracking system may be modified to allow for tilting of the image receptor. In the third embodiment, additional position sensors may be provided in the image receptor to track the angular tilt along the longitudinal axis, the transverse axis, or both axes, of the image receptor. In operation, the DSA is manually positioned in substantially the same fashion as described above with reference to FIG. 1. However, when the system controller calculates the optimal alignment and height of the image receptor, angular tilt of the image receptor may also taken into account. Thus, when the system controller sends the optimal calculated position to the motor drive of the image receptor, the motor drive may position the longitudinal position, the transverse position, the height, and the angular tilt of the image receptor to the calculated location. Increasing the range of motion of the image receptor to include axial tilting of the image receptor may further increase the ability of the tracking system 100 to take complete and accurate images with low attenuation or anatomical cut-off.

Thus, the automated receptor tracking system 100 presented in the present invention combines the optimal alignment properties of a direct alignment system with the flexibility of an indirect alignment system. Additionally, the present invention presents a positioning control system that allows for quick and precise alignment of a diagnostic source assembly and an image receptor. Therefore, the present invention may reduce the total imaging time and increase cost effectiveness by reducing the number of retakes required to obtain a satisfactory X-ray image. Reducing retakes may also result in decreased exposure to radiation by the patient being imaged which is healthier to the patient.

Additional information regarding the present invention may be found in the pending patent application entitled "Imaging System with X-ray Beam Anulation Compensation," application Ser. No. 09/615,475, which was filed with the USPTO on Jul. 13, 2000, and is hereby incorporated by reference in its entirety.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for calculating an optimal position of an image receptor based on the position of a manually positioned diagnostic source assembly, said system including:
   a system controller for receiving positional data from said diagnostic source assembly and calculating an optimal position for said image receptor based on said positional data received from said manually positioned diagnostic source assembly on a per-exposure basis.

2. The system of claim 1 wherein the optimal position for said image receptor is transmitted to a motor drive by said system controller.

3. The system of claim 1 wherein positional sensors on said diagnostic source assembly transmit said positional data from said diagnostic source assembly to said system controller.

4. The system of claim 1 wherein said image receptor includes positional sensors for transmitting positional data of said image receptor to said system controller.

5. The system of claim 1 wherein said system controller includes a microprocessor for calculating said optimal position.

6. A system for automatically positioning an image receptor in a medical imaging system, said system including:
   a manually positioned diagnostic source assembly;
   an automatically positioned image receptor;
   a system controller for receiving positional data from said manually positioned diagnostic source assembly, calculating an optimal position for said automatically positioned image receptor with respect to the position of said manually positioned diagnostic source assembly and transmitting said optimal position to a motor drive; and
   a motor drive for automatically positioning said image receptor in response to said optimal position.

7. The system of claim 6, wherein said system controller calculates said optimal position on a per-exposure basis.

8. The system of claim 6 wherein said manually positioned diagnostic source assembly includes at least one position sensor for transmitting the lateral orientation of said manually positioned diagnostic source assembly to said system controller.

9. The system of claim 6 wherein said manually positioned diagnostic source assembly includes at least one position sensor for transmitting the longitudinal orientation of said manually positioned diagnostic source assembly to said system controller.

10. The system of claim 6 wherein said manually positioned diagnostic source assembly includes at least one position sensor for transmitting the vertical orientation of said manually positioned diagnostic source assembly to said system controller.

11. The system of claim 6 wherein said manually positioned diagnostic source assembly includes at least one position sensor for transmitting the angular orientation of said manually positioned diagnostic source assembly to said system controller.

12. The system of claim 6 wherein said image receptor includes position sensors for transmitting the longitudinal position of said automatically positioned image receptor to said system controller.

13. The system of claim 6 wherein said image receptor includes position sensors for transmitting the height of said automatically positioned image receptor to said system controller.

14. The system of claim 6 wherein said image receptor includes position sensors for transmitting the axial tilt of said automatically positioned image receptor to said system controller.

15. A method for automatically positioning an image receptor, said method including the steps of:

calculating an optimal image receptor position based on the position of a manually positioned diagnostic source assembly; and automatically positioning said image receptor based on said optimal image receptor position.

16. The method of claim 15 further including the step of verifying the position of said image receptor at said optimal image receptor position.

17. The method of claim 15 further including the step of manually overriding a motor drive to manually position said image receptor.

18. A method for calculating an optimal position of an image receptor based on the position of a manually positioned diagnostic source assembly, said method including the steps of:

receiving positional data from said manually positioned diagnostic source assembly; and calculating an optimal position of said image receptor based on the position of aid manually positioned diagnostic source assembly using a system controller per-exposure basis.

19. The method of claim 18 further including the step of transmitting said positional data from said diagnostic source assembly using positional sensors.

20. The method of claim 18 further including the step of transmitting said optimal position calculated by said system controller to a motor drive.

21. The method of claim 18 wherein said system controller includes a microprocessor.

22. The method of claim 15, wherein said optimal image receptor position is calculated on a per-exposure basis.

* * * * *